United States Patent [19]
Stolzy

[11] 3,962,572
[45] June 8, 1976

[54] RATE DIVIDER

[75] Inventor: Albert Donald Stolzy, Encino, Calif.

[73] Assignee: International Telephone and Telegraph Corporation, New York, N.Y.

[22] Filed: June 19, 1975

[21] Appl. No.: 588,641

Related U.S. Application Data

[62] Division of Ser. No. 524,043, Nov. 15, 1974, Pat. No. 3,918,292.

[52] U.S. Cl............................. 235/156; 235/92 PE; 328/48; 340/146.2
[51] Int. Cl.² ........................................ H03K 21/36
[58] Field of Search............. 235/156, 164, 92 DM, 235/92 PE, 92 CA; 328/48; 340/146.2

[56] References Cited
UNITED STATES PATENTS

| | | | |
|---|---|---|---|
| 3,369,183 | 2/1968 | Mester................................. | 328/48 |
| 3,719,897 | 3/1973 | Tarv.................................... | 328/48 X |
| 3,818,354 | 6/1974 | Tomisawa et al.................. | 328/48 X |
| 3,824,378 | 7/1974 | Johnson et al.................. | 235/92 PE |
| 3,824,379 | 7/1974 | Tomisawa et al.............. | 235/92 PE |

*Primary Examiner*—David H. Malzahn
*Attorney, Agent, or Firm*—A. Donald Stolzy

[57] ABSTRACT

A vibration gravitometer having leaf spring vanes located in respective cells in a thermally conductive block. Each cell contains a different gas at ambient atmospheric temperature and pressure. One cell contains air, the other a gas, the gravity of which is to be monitored, "gravity" being defined as the ratio of the density of the gas to the density of air at the same temperature and pressure. The gravity of one specific gas of constant composition is a constant. The vanes are vibrated at the same or different frequencies dependent upon the air and gas densities. These frequencies are multiplied and combined in a digital calculator that utilizes a frequency-time reciprocal to divide. A readout circuit multiplies the output of the calculator by a constant of proportionality and indicates the gravity.

1 Claim, 29 Drawing Figures

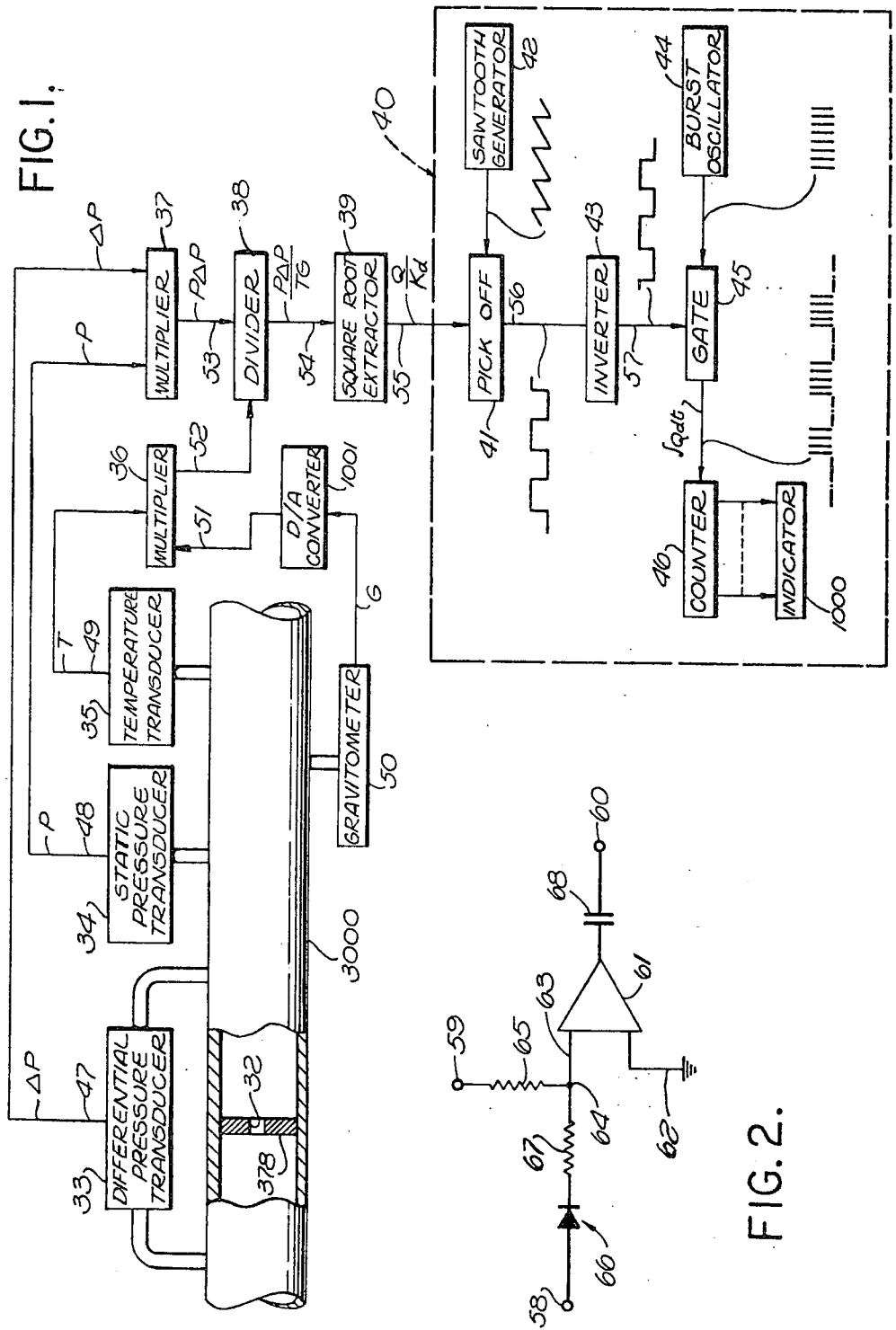

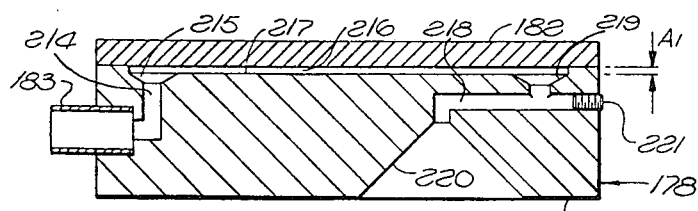
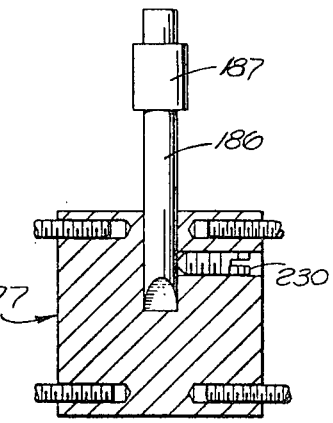
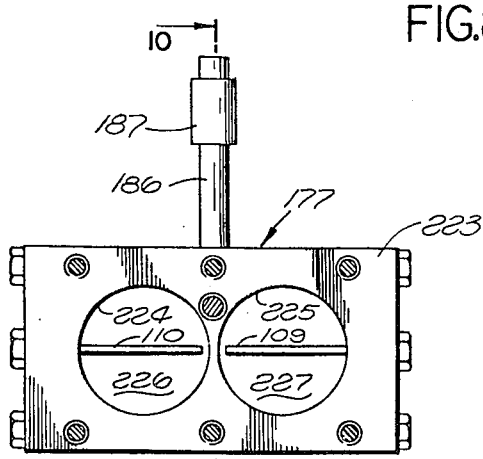
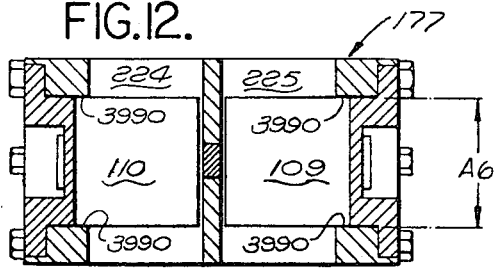
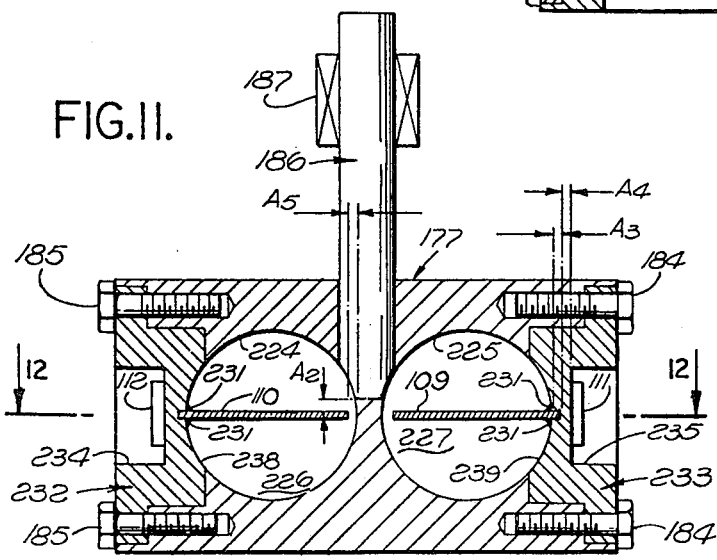
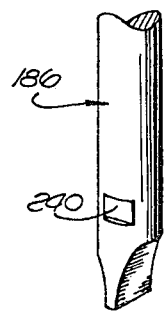

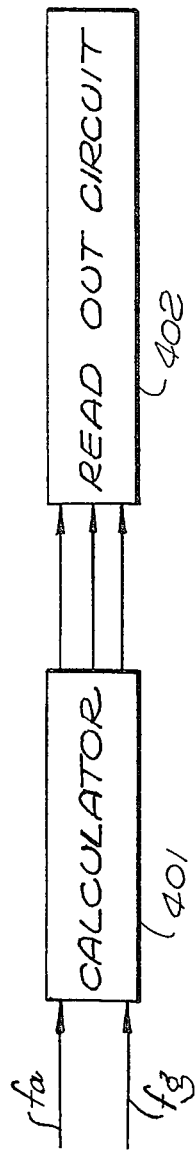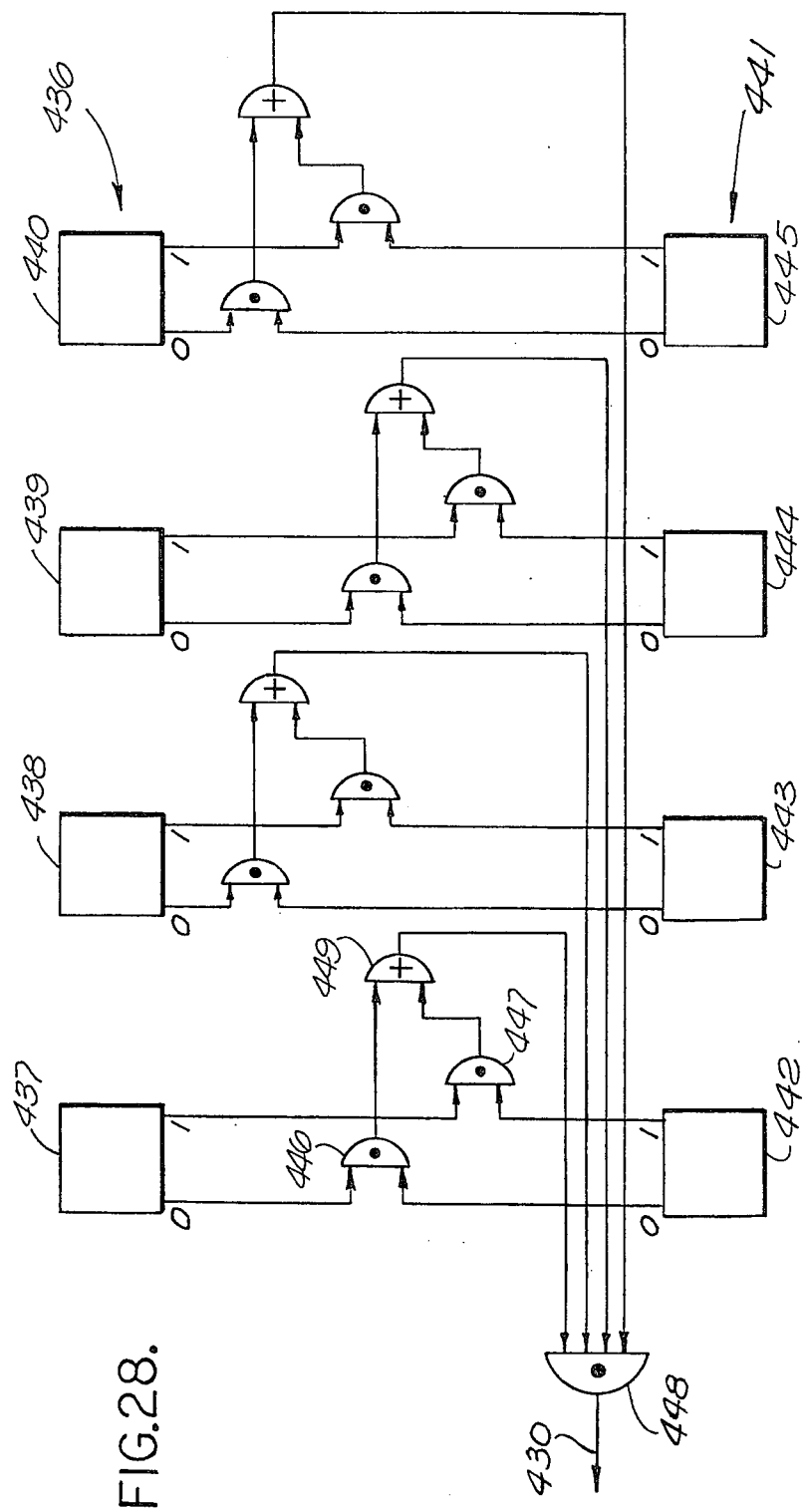
FIG. 25.
FIG. 28.

RATE DIVIDER

This is a division of copending application Ser. No. 524,043 filed Nov. 15, 1974, now issued U.S. Pat. No. 3,918,292. The benefit of the filing date of said copending application is, therefore, hereby claimed.

BACKGROUND OF THE INVENTION

This invention relates to continuously variable frequency division, and more particularly to a rate divider.

In the past it has been difficult, if not impossible, to derive, by an inexpensive and rapidly responding digital device, a ratio of one time period to another. In the prior art, this has resulted in the use of equipment which has considerable error. For example, such equipment might have an error of in excess of 1 percent over a range of less than 10 percent. This is unfortunate in that the computation of gravity, e.g. the ratio of the density of a gas of interest to that of air at the same temperature and pressure, can require a digital device to derive the ratio of one time period to another.

SUMMARY OF THE INVENTION

In accordance with the present invention, the above-described and other disadvantages of the prior art are overcome by employing a new device called a rate divider herein.

In accordance with another feature of the invention the rate divider is incorporated into a gravitometer to produce a digital output directly proportional to the ratio of one timer period to another. The gravitometer and rate divider of the present invention are, moreover, inexpensive and have rapid dynamic responses. Further, both can provide outputs of any desired accuracy.

The gravitometers of the present invention have utility when used by themselves or in flowmeters, process controllers or otherwise. For example, the output of a gravitometer constructed in accordance with the present invention may be connected to one or more process controllers, or to a D.C. milliammeter or recorder calibrated in gravity, or any other apparatus.

Different natural gases are frequently blended to achieve a desired BTU content based on the gas gravities.

A gravity indication is, thus, useful in estimating the BTU content of natural gas. It can be used in determining performance under gas delivery contracts specifying BTU content. Further, estimated BTU content is also fequently used for billing purposes.

As will be understood from the foregoing, automatic process controllers can be operated from the gravitometers of the present invention to maintain automatically any desired gravity or BTU content.

The above-described and other advantages of the present invention will be better understood from the following detailed description when considered in connection with the accompanying drawings.

BRIEF DESCRIPTION OF THE DRAWINGS

In the drawings which are to be regarded as merely illustrative:

FIG. 1 is a diagrammatic view of a flowmeter;

FIG. 2 is a schematic diagram of a pickup shown in FIG. 1;

FIG. 8 is a horizontal sectional view taken on the line 8—8 shown in FIG. 7;

FIG. 9 is a vertical sectional view taken on the line 9—9 shown in FIG. 5;

FIG. 10 is a vertical sectional view taken on the line 10—10 shown in FIG. 9;

FIG. 11 is a vertical sectional view taken on the line 11—11 shown in FIG. 5;

FIG. 12 is a horizontal sectional view taken on the line 12—12 shown in FIG. 11;

FIG. 13 is a perspective view of a ferromagnetic rod shown in FIGS. 5, 9, 10 and 11;

FIG. 25 is a block diagram of a calculator and readout circuit shown in FIG. 4;

FIG. 28 is a detailed block diagram of a coincidence gate shown in FIG. 26; and

DESCRIPTION OF THE PREFERRED EMBODIMENT

The Flowmeter of FIG. 1

Figure 3:
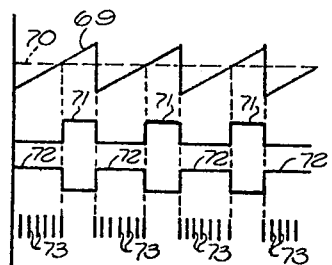
FIG. 3 is a graph of a group of waveforms characteristic of the operation of the flowmeter shown in FIG. 1.

Although the gravitometer of the present invention will have utility in a great many systems or by itself, one use thereof is in a flowmeter, to be described.

It is well known in the prior art that the total flow $\int Q\,dt$ where $t$ is time and $Q$ is the volume rate of gas flow per unit time, $Q$ being measured in standard cubic feet. This standard cubic feet (at, for example, 14.7 pounds/cubic feet pressure and 68° F.) of a gas in a pipeline may be calculated from the following equation (1) defining mass flow rate Q.

$$Q = K_a \sqrt{\frac{P \Delta P}{T_1 G}} \qquad (1)$$

where,

P is the static pressure in a pipeline 3000 shown in FIG. 1, $\Delta P$ is the differential pressure across an orifice 32, $T_1$ is the absolute temperature of the gas, and G is the "gravity" of the gas.

The gravity, G, of a gas is defined by $$G = \rho_g/\rho_a \qquad (2)$$

where, $\rho_g$ is the density of the gas at a predetermined temperature and at a predetermined pressure, and $\rho_a$ is the density of air at the same said predetermined temperature and predetermined pressure.

It is interesting to note that G is substantially "independent" of temperature and pressure. That is, for the same gas, the value of G will be the same regardless of which "predetermined temperature" and "predetermined pressure" it is measured. The proof for this characteristic follows.

Boyle's law and Charles's law may be combined into the single expression $$PV/T_1 \qquad (3)$$

which is equal to a constant. Hence, $$PV = MRT_1 \qquad (4)$$

where,

P is pressure,

V is volume,

M is mass,

R is the gas constant, and $T_1$ is absolute temperature.

If $\rho$ is density, then $$\rho = M/V \qquad (5)$$

Thus, combining (6) and (7), $$\rho = K_1 P/T_1 \qquad (6)$$

where, $$K_1 = 1/R \qquad (7)$$

Equations (10) and (11) are analogous to (8) for a gas, g, of interest and air, a.

$$\rho_g = \frac{K_{1g}P_g}{T_{g1}} \qquad (8)$$

$$\rho_a = \frac{K_{1a}P_a}{T_{a1}} \qquad (9)$$

Dividing (10) and (11) and assuming $P_g = P_1$ and $T_g = T_a$, $$\rho_g/\rho_a = K_{1g}/K_{1a} \qquad (10)$$

Combining (4), (8) and (12), $$G = R_a/R_g \qquad (11)$$

Equation (13), thus, indicates that G is truly "independent" of which set of temperature and pressure conditions are selected.

Equation (3) may be proven as follows. The flow, $Q_s$, through an orifice is $$Q_s = K_2 A \sqrt{2gH_a} \qquad (12)$$

where, $K_2$ is a constant,

A is the orifice area, g is acceleration due to the earth's gravity, and $H_g$ is the differential pressure head in feet across the orifice.

To convert the differential head to inches of air, $$H_a = H_g \rho_g / 12 \rho_a \qquad (13)$$

Hereinafter, the 68° F. and the 14.7 pounds/square inch will be referred to as "standard temperature and pressure $T_a$ and $P_a$, respectively."

Equation (10) can, thus, be divided by equation (11) as follows:

$$\rho = K_{1a}GP/T_1 \qquad (14)$$

where,

P is equal to $P_g$, $T_1$ is equal to $T_g$, and $\rho$ is equal to $\rho_g$.

Substituting $\rho = \rho_g$ into (15), (16) into the resultant, one obtains $$H_g = H_a \rho_a T_1 / 12 K_{1a} GP \qquad (15)$$

Substituting (17) into (14), one obtains $$Q_s = K_2 A \sqrt{\frac{2gH_a \rho_a T_1}{12 K_{1a} GP}} \qquad (16)$$

Thus, $$Q_s = K_3 \sqrt{\frac{H_a \rho_a T_1}{GP}} \qquad (17)$$

where, $$K_3 = K_2 A \sqrt{\frac{2g}{12K_{1a}}} \qquad (18)$$

From expression (5), $$PQ/T = P_a Q_a / T_{a1} \qquad (19)$$

Thus, $$Q_a = PQT_{a1}/T_1 P_a \qquad (20)$$

Combining (19) and (22), $$Q = K_3 \sqrt{\frac{H_a \rho_a T_1}{GP}} \times \frac{PT_{a1}}{TP_a} \qquad (21)$$

and $$Q = K \sqrt{\frac{P\Delta P}{TG}} \qquad (22)$$

where, $$K_a = K_3 T_{a1}/P_a \qquad (23)$$

and $\Delta P$ is equal to $H_1\rho_a$ (pressure equals height times density).

The embodiment of FIG. 1 mechanizes equation (3) for continuously indicating total volume flow in standard cubic feet.

In FIG. 1, a portion of a pipeline is indicated at 3000 having a disc 378 fixed therein to provide an orifice 32. A differential pressure transducer 33 senses the difference between the pressures on opposite sides of orifice 32. A static pressure transducer 34 senses the pressure on one side of orifice 32. A temperature transducer 35 senses the temperature on one side of the orifice 32.

In FIG. 1, a multiplier 36, a multiplier 37, a divider 38 and a square root extractor 39 are provided. An output circuit 40 is connected from the output of square root extractor 39. Output circuit 40 includes a pickoff 41, a saw-tooth generator 42, an inverter 43, a burst oscillator 44, a gate 45 and a counter 46.

Differential pressure transducer 33 produces a D.C. current on an output lead 47 which is directly proportional to the difference between the pressures on opposite sides of the orifice 32.

Static pressure transducer 34 produces a D.C. current on an output lead 48 directly proportional to the pressure on one side of orifice 32. Temperature transducer 35 produces a D.C. current on an output lead 49 directly proportional to the temperature of the gas inside pipeline 3000 on one side of orifice 32.

A gravitometer 50 is connected from pipeline 3000 on one side of orifice 32 to produce a D.C. output current on an output lead 51 of a digital-to-analog converter 1001 directly proportional to the gravity of the gas in pipeline 3000.

Multiplier 36 is connected from leads 49 and 51. The output of multiplier 36 is impressed upon an output lead 52 which is connected to divider 38. Multiplier 36 then produces an output current in lead 52 which is directly proportional to the product of the outputs of temperature transducer 35 and gravitometer 50.

Multiplier 37 is connected from both of the pressure transducers 33 and 34 to divider 38. Multiplier 37 has an output lead 53, the current in which is directly proportional to the product of the current outputs of the pressure transducers 33 and 34. Divider 38 has an output lead 54 which carries a D.C. voltage directly proportional to the output of multiplier 37 divided by the output of multiplier 36. Divider 38 may, if desired, include a current-to-voltage converter at its output. A current-to-voltage converter, for example, may be simply a resistor connected from the output of divider 38 to ground.

Notwithstanding the foregoing, any component part of the invention employed to produce a current analog may be employed to produce a voltage analog.

Square root extractor 39 has an output lead 55 upon which a D.C. voltage is impressed which is directly proportional to the square root of the output of divider 38.

Pickoff 41 has an output lead 56 upon which a square wave is impressed. This square wave is generated by comparing the amplitude of the saw-tooth output of generator 42 with the amplitude of the D.C. voltage on lead 55.

Inverter 43 is connected over an output lead 57 to gate 45. Inverter 43 inverts the square wave output of pickoff 41.

It is to be noted that the dimensions of a square wave are conventionally vertical in volts and horizontal in time. The word "square," thus, has no reference to any particular relationship between the amplitude and period of such a wave. The phrase "square wave" is, therefore, hereby defined for use herein and in the claims to mean "a rectangular wave" or vice versa.

Burst oscillator 44 produces output pulses at a constant rate and at a pulse repetition frequency (PRF) which is large in comparison to the PRF of the square wave appearing on inverter output lead 57. Gate 45 is opened during the positive pulses of the square wave on lead 57, and passes pulses from the burst oscillator 44 to counter 46 during the pulses of the square wave on lead 57.

All of the parts shown in FIG. 1 may be entirely conventional, if desired, except gravitometer 50. Gravitometer 50 is constructed in accordance with the present invention, as will be explained.

Multipliers 36 and 37 may be entirely conventional voltage or current multipliers, if desired. Divider 38 may be an entirely conventional divider, if desired. Square root extractor 39 may be an entirely conventional square root extractor or function generator, if desired.

Saw-tooth generator 42, gate 45, inverter 43 and counter 46 may all be entirely conventional. Pickoff 41 may also be entirely conventional, if desired.

If desired, an indicator 1000 connected from counter 46 may be calibrated in total volume flow in standard cubic feet. Counter 46, if desired, may be an entirely conventional binary counter.

In FIG. 2, pickoff 41 is shown including input terminals 58 and 59, and an output terminal 60. An amplifier 61 is also shown in FIG. 2 connected to ground at 62 and having an input lead 63 connected to a summing junction 64. A resistor 65 is connected from terminal 59 to junction 64. A diode 66 and a resistor 67 are connected in series in that order from terminal 58 to junction 64. A capacitor 68 is connected from the output of amplifier 61 to terminal 60.

In FIG. 1, terminal 58 would be connected from saw-tooth generator 42. Terminal 59 would be connected from square root extractor 39. Output terminal 60 would be connected to inverter 43. The voltage supplied to terminal 59 by square root extractor 39 would be a negative voltage. The output signal of saw-tooth generator 42 would be a positive going voltage. It would begin at ground and increase from there to its peak value. When the potential at terminal 58 equals or slightly exceeds the negative potential at 59, amplifier 61, if it is a high gain amplifier having a gain of several hundred thousand, will produce a square wave output by being driven into saturation. The pulses at the output of amplifier 61 will then have a pulse width directly proportional to the output voltage of square root extractor 39.

The saw-tooth output voltage of saw-tooth generator 42 is indicated at 69 in FIG. 3. The corresponding positive magnitude of the negative output voltage of square root extractor 39 is indicated at the horizontal line 70 in FIG. 3. The horizontal level of line 70 may vary from time to time, but will generally not vary as fast as the PRF of the saw-tooth voltage.

As shown in FIG. 3, pulses 71 are produced at the output of pickoff 41 in FIG. 1 which have a time width determined by the end of each saw-tooth 69 and a beginning which occurs where the inclined portion of each saw-tooth crosses line 70.

As shown in FIG. 3, inverter 43 has output pulses 72, the time width of which is directly proportional to the amplitude of the output signal of square root extractor 39. In FIG. 3, the portion of the output pulses of burst oscillator 44, which are counted by counter 46, are indicated at 73.

OPERATION OF THE FLOWMETER OF FIG. 1

In FIG. 1, the transducers 33, 34 and 35 produce differential pressure, static pressure and temperature analogs. The pressure analogs are multiplied together by multiplier 37. The temperature analog is multiplied by the gravity analog appearing on the output lead 51 of converter 1001 by multiplier 36. The output of multiplier 37 is divided by the output of multiplier 36 in divider 38. The square root of the output of divider 38 is taken by square root extractor 39. The analog output of square root extractor 39 is then integrated in output circuit 40. Saw-tooth generator 42, pickoff 41 and inverter 43 produce a time analog at the output of inverter 43 of the output of square root extractor 39. This is converted to a digital number which is accumulated in binary counter 46, this digital number representing total volume flow in standard cubic feet. This digital number is indicated by indicator 1000 which has one lamp for each flip-flop or stage in counter 46 or is digital and calibrated.

Figure 4:
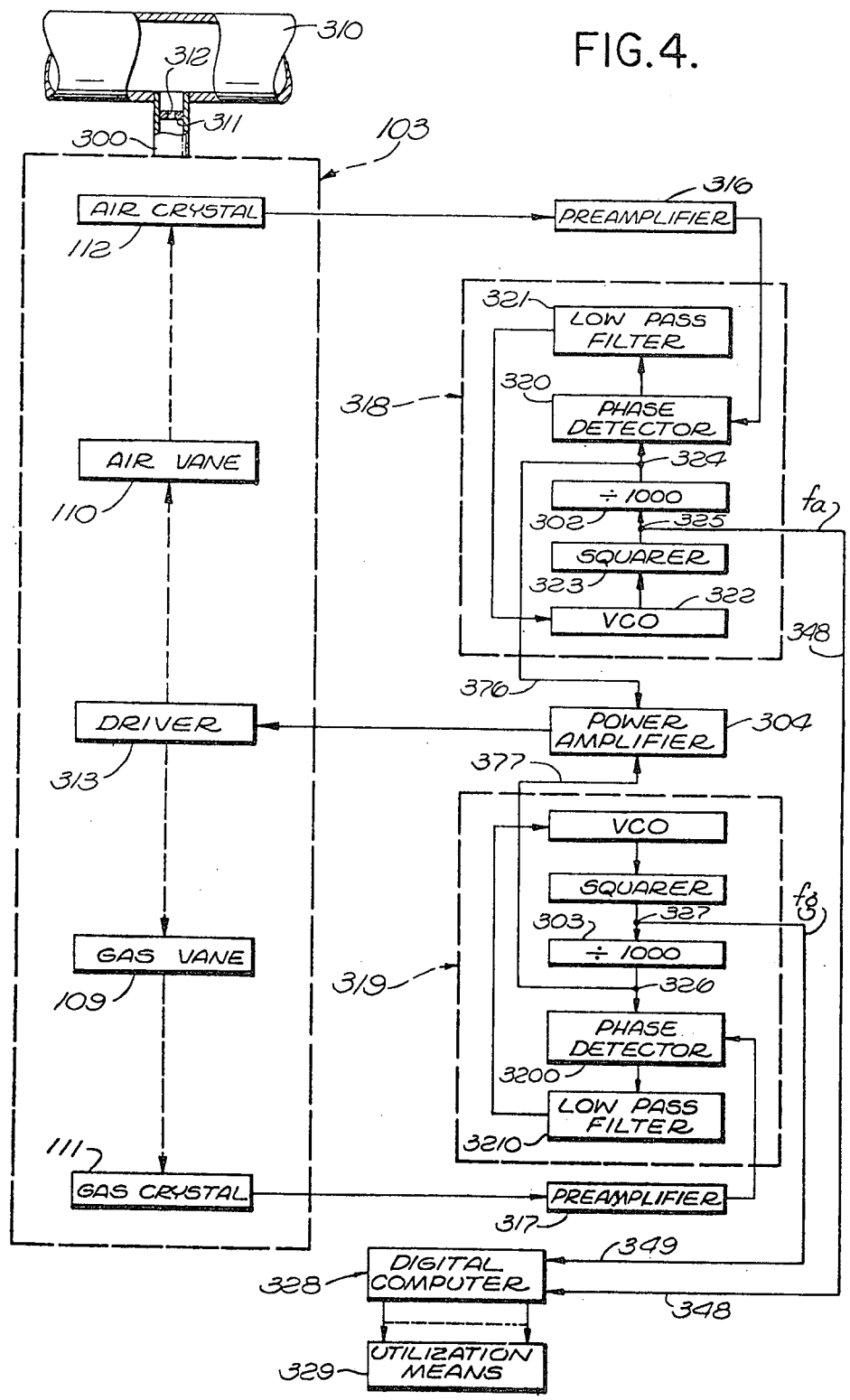
FIG. 4 is a diagrammatic view of a gravitometer constructed in accordance with the present invention.

The Gravitometer of the Present Invention Illustrated in FIG. 4

In FIG. 4, a pipeline is illustrated at 310 having a conduit 300 connected therefrom to a twin cell assembly 103. Conduit 300 has a disc 311 sealed therein that has an orifice 312 to admit a sample of the gas flowing in pipeline 310 to assembly 103 at a relatively low flow rate and at a relatively low pressure.

Assembly 103 includes a gas vane 109 which vibrates in the gas sample, and an air vane 110 which vibrates in air at ambient temperature and pressure.

Neither of the vanes 109 and 110 vibrate naturally. There are losses. Vanes 109 and 110 must, thus, be driven. They are driven by a driver 313. Driver 313 forms a link in two combined closed loop electromechanical oscillators which oscillate both of the vanes 109 and 110 *unexpectedly* at *different* frequencies and at *different* rate of change of frequencies, the former being functions of respective densities.

It is a striking thing that the density of the gas and air in which vanes 109 and 110, respectively, vibrate are unexpected functions of the vane frequencies and periods.

The frequency and period of the vibration of air vane 110 is detected by a piezoelectric air crystal 112. Similarly, the frequency and period of the vibration of gas vane 109 is detected by a piezoelectric gas crystal 111. The output of air crystal 112 is connected to the input of a preamplifier 316. The output of gas crystal 111 is connected to the input of a preamplifier 317.

The output of preamplifier 316 is connected to the input of a phase lock loop 318. The output of preamplifier 317 is connected to the input of phase lock loop 319. Each of the phase lock loops 318 and 319 may or may not be identical to each other, if desired. Each of the phase lock loops 318 and 319 mmay be entirely conventional including adaptations which they have to produce two square wave output signals each, all four of such signals normally having different frequencies. All four output signals may have a mark-to-space ratio of unity although that is not always necessary and may never be necessary. Phase lock loop 318 has an adaptation which makes it a frequency multiplier by the addition of a divide-by-1,000 divider 302. Similarly, phase lock loop 319 has a divide-by-1,000 divider 303 which makes phase lock loop 319 a frequency multiplier as well.

In production, it is impossible to make two air vanes precisely alike. It is also impossible to make two gas vanes precisely alike. As will be explained, each vane is calibrated independently. It is impossible to predict what the vibrational frequency of air vane will be in advance. Thus, all the numerical values given herein are typical. However, these values could not be predicted with the accuracy desired for any given vane. The air vane 110 might have a vacuum frequency of 316.000 Hz. The air vane might have a frequency of 314.000 Hz. for a dry air density of 0.001205 gram per milliliter at 20° C. and at 760 millimeters of Mercury. Call this density $d_c$. For a density of $2d_c$, the air vane may have a frequency of 312.025 Hz.

Again, typically, the gas vane 109 may have a vacuum frequency of 314.000 Hz. At $d_c$, the gas vane frequency may be 312.000 Hz.

Phase lock loop 318 has a phase detector 320, the output of which is impressed upon a low pass filter 321. Low pas filter 321 may or may not have an amplifier. Similarly, amplifiers and inverters may be omitted or added throughout this disclosure, as desired.

The loop is closed by connection from low pass filter 321 through a voltage controlled oscillator (VCO) 322, a squarer 323, divider 302 to phase detector 320.

Squarer 323 may be omitted in some or all cases. It is conventional to employ a VCO which has a square wave output.

Phase lock loop 318 has an output junction 324 connected from the output of divider 302, and an output junction 325 connected from the output of squarer 323. Similarly, phase lock loop 319 has an output junction 326, and an output junction 327.

Because both of the phase lock loops 318 and 319 may be identical, the remaining details of phase lock loop 319 will not be described.

The output from junction 324 in phase lock loop 318 is connected to one input of a power amplifier 304. Similarly, the output junction 326 of phase lock loop 319 is connected to the other input of power amplifier 304.

The power amplifier 304 has an output which is connected to driver 313 in assembly 103.

Junctions 325 and 327 in phase lock loops 318 and 319 are connected to a digital computer 328 which, in turn, is connected to utilization means 329.

In accordance with the foregoing, the frequencies appearing at junctions 324 and 326 in phase lock loops 318 and 319, respectively, for a gas density of $d_c$ and an air density of $d_c$ may, for example, be 312.000 Hz. and 314.000 Hz., respectively. On the other hand, the corresponding frequency of the square wave having the legend $f_a$ will have a frequency for a density $d_c$ of 314,000 Hz. The lead having the legend $f_g$ will have a corresponding frequency for gas density of $d_c$ equal to 312,000 Hz.

In accordance with the foregoing, $f_a$ is directly proportional to or equal to the air vane frequency depending upon whether the multiplication factor of frequency multiplier 318 is something other than 1.0 or 1.0, respectively. Similarly, $f_a$ is directly proportional to or equal to the gas vane frequency depending upon whether the multiplication factor of frequency multiplier 319 is something other than 1.0 or 1.0, respectively.

Digital computer 328 converts the inputs thereto labeled $f_a$ and $f_g$ to a digital number which is directly proportional to the gravity of the gas flowing in pipeline 310.

The instrument as illustrated in FIG. 4 may be sold without the utilization means 329. The utilization means 329 may take many forms. The gravitometer of the present invention may be used in larger computation systems. It may be used as gravitometer 50 in the flowmeter of FIG. 1 or in any other systems. It may be employed in process control systems. Utilization means 329 may, thus, be a flowmeter, a process control system, simply means to indicate the gravity of the gas flowing in pipeline 310 or otherwise. For this reason, the phrase "utilization means" is defined for use herein and for use in the claims to mean a flowmeter, another system, a process control system, an indicator, or otherwise.

In FIG. 4, low pass filter 321 and low pass filter 3210 may be identical. One or both or neither may or may not have a cut-off frequency below the second harmonic of the output signals of the outputs of phase detectors 320 and 3200 but may conveniently be so constructed with a cut-off frequency below the said second harmonic and above the fundamental, which is, in the cases of phase detectors 320 and 3200, perphas midway between 300 and 400 Hz.

In FIG. 4, each of the phase detectors 320 and 3200 may be conventional or may be four quadrant analog multipliers. See Neil Marshall, U.S. Pat. No. 3,783,259.

The Twin Cell Assembly 103 Illustrated in FIGS. 5–15

Figure 5:
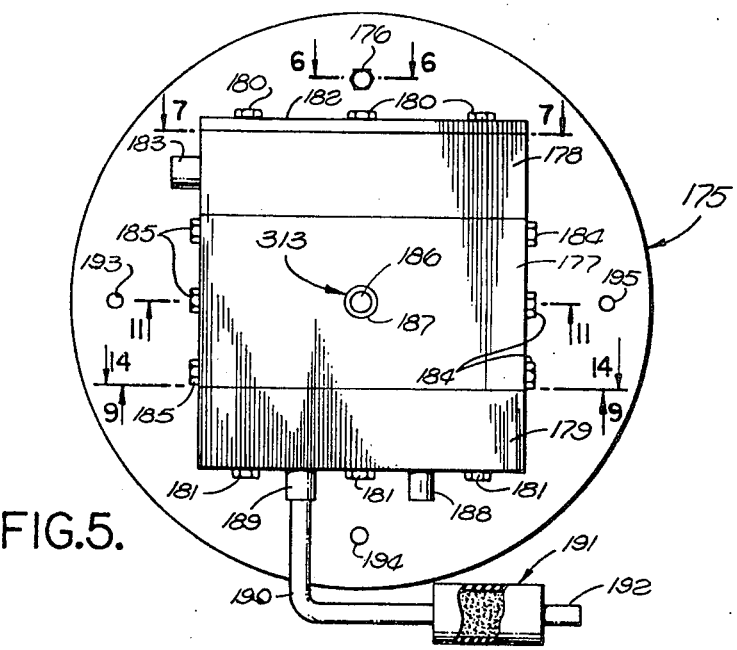
FIG. 5 is a top plan view of a twin cell assembly indicated diagrammatically in FIG. 4.

A top plan view of assembly 103 is shown in FIG. 5 including a supporting plate 175, a supporting bolt 176, a central block 177, an inlet block 178 and an outlet block 179. Inlet block 178 is fixed to central block 177 by six cap screws 180, only three of which are shown in FIG. 5. Similarly, outlet block 179 is fixed to central block 177 by six cap screws 181. A cover plate 182 is positioned between the heads of screws 180 and inlet block 178. Inlet block 178 has an inlet ferrule 183 into which conduit 300 may be inserted and sealed.

Four cap screws 184 fix a subassembly to block 177. Similarly, four cap screws 185 fix another subassembly to block 177. Both of the said subassemblies will be described hereinafter.

Driver 313 includes a ferromagnetic rod 186 which projects into and is fixed relative to block 177, as will be described. A driver coil 187 is fixed relative to rod 186 therearound.

Outlet block 179 carries gas and air vent ferrules 188 and 189, respectively, that are fixed relative thereto. A conduit 190 is inserted into ferrule 189 and may be sealed therein, if desired, A dessicator 191 is connected from conduit 190 and has a vent tube 192 allowing air to pass back and forth through dessicator 191 from the atmosphere into and out of block 177, respectively.

Only one bolt 176 is shown in FIG. 5. However, four bolts are preferably employed. Other bolts would pass through holes 193, 194 and 195 in plate 175, as shown in FIG. 5.

Figure 6:
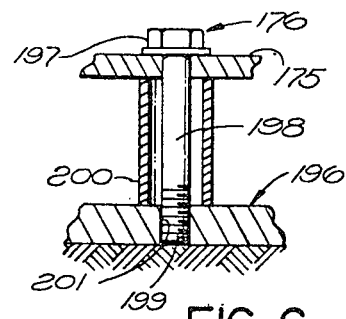
FIG. 6 is a vertical sectional view taken on the line 6—6 through a mounting bolt shown in FIG. 5.

All the structures shown in FIG. 6 are fixed relative to each other. A plate 196 is provided below plate 175. Bolt 176 has a head 197 that rests on top of plate 175, a shank 198 which is slidable therethrough and a threaded lower end 199 which is treaded into plate 196. A cylindrical spacer 200 is held in axial compression between plates 175 and 196, bolt shank 198 extending through the center of spacer 200.

Plate 196 has four threaded holes 201, only one of which is shown in FIG. 6. The other three holes lie substantially in registration with holes 193, 194 ad 195, respectively, of plate 175.

Figure 7:
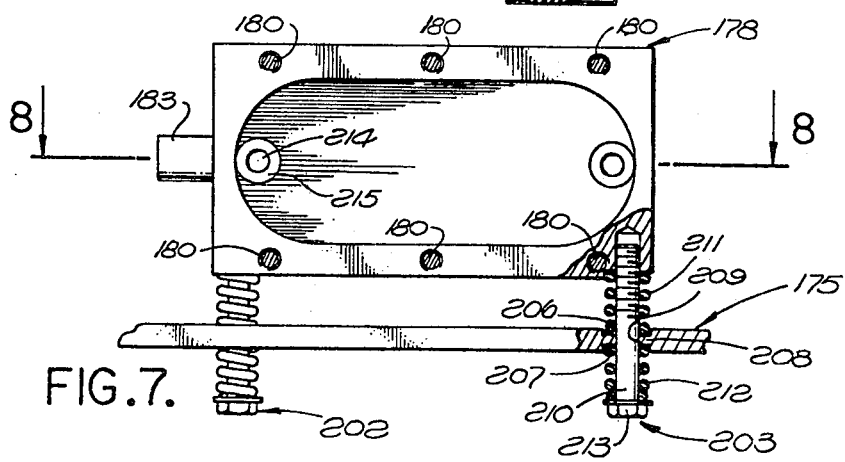
FIG. 7 is a vertical sectional view taken on the line 7—7 shown in FIG. 5.

As shown in FIG. 7, block 178 has two cap screws 202 and 203 fixed relative thereto. The structure immediately surrounding screw 202 is substantially identical to that surrounding screw 203. Thus, the structure immediately surrounding screw 203 will be the only structure described. The same is true of the structure surrounding screws 204 and 205 in FIG. 14. In FIG. 7, plate 175 is recessed at 206 and 207. Plate 175 has a web 208 which separates the recesses 206 and 207. Web 208, itself, has an opening 209 therethrough through which the shank 210 of screw 203 projects. Screw shank 210 is, thus, slidable through opening 209. A spring 211 is trapped and held in compression between web 208 and the lower end of block 178, as viewed in FIG. 7. A spring 212 is trapped and held in compression between web 208 and the head 213 of screw 203. A resilient mounting is, thus, provided for all the structure above plate 175 which is fixed relative to screws 202, 203, 204 and 205.

Screws 180, shown in FIGS. 5 and 7, are slidable through corresponding holes in plate 182 and block 178 and threaded part way into block 177.

As shown in FIG. 8, gas can be introduced into block 178 through a conduit 214 therein through a frustoconical port 215 into a thin space 216. A number of the relative dimensions shown herein may be employed, if desired. Space 216 is defined by a recess 217 in block 178 shown in FIG. 8. Gas can then enter a conduit 218, shown in FIG. 8, through another frusto-conical port 219. A larger frusto-conical outlet surface 220 then lies in communication with conduit 218. One end of conduit 218 is closed by a screw 221 threaded thereinto and sealed therein.

As shown in FIG. 8, the depth of recess 217 is quite small and is represented by the dimension A1. It is, thus, possible to equalize the temperatures of the gas and air in block 177, to be described. Preferably, blocks 177, 178 and 179 are made of 302 stainless steel or are made of 303 stainless steel. Blocks 177, 178 and 179 may be made of these or any other conventional materials which have a fairly good thermal conductivity and are nomagnetic. However, it makes little difference whether or not any of the cap screws shown in FIGS. 5, 6, 7 and 14 are or are not magnetic. They may or may not be magnetic, as desired.

The lower face 222 of block 178, shown in FIG. 8, fits on the face opposite 223 off block 177, shown in FIG. 9, with the cylindrical surface 225, shown in FIG. 9, having an axis that is the same as that of conical surface 220, shown in FIG. 8. The width and heights of blocks 177, 178 and 179 are all the same. They also are all aligned as in FIG. 5.

As shown in FIG. 9, another cylindrical surface is provided at 224. Cylindrical holes 224 and 225 extend completely through the width of block 177, spaces inside thereof being mostly defined by the surfaces 224 and 225. These spaces may be hereinafter referred to as the gas chamber 227 and the air chamber 226. Note that surface 222 in FIG. 8 closes one end of air chamber 226.

Air vane 110 extends into air chamber 226. Gas vane 109 projects into gas chamber 227.

As shown in FIG. 10, rod 186 is fixed in block 177 by a set screw 230. Rod 186 and set screw 230 may also be sealed therein, if desired. As shown in FIG. 11, vanes 109 and 110 are silver soldered at 231 to respective circular inserts 233 and 232 fixed relative to block 177 by screws 184 and 185, respectively.

Inserts 232 and 233 have respective recesses 234 and 235 at the bottom of which piezoelectric crystals 112 and 111 are bonded with any conventional agent such as a conventional epoxy.

A device 301, to be described further, is fixed relative to insert 232.

In FIG. 11, note will be taken that the lower end of rod 186 is disposed slightly above the upper surface of vane 110, as viewed in FIG. 11.

If desired, vanes 109 and 110 may be identical. Moreover, the upper and lower surfaces thereof may lie in two corresponding single planes. Certain symmetry will be evident from FIGS. 11 and 12.

The location of the lower end of rod 186 above the vanes is indicated at A2 in FIG. 11.

As shown in FIG. 11, inserts 232 and 233 have cylindrical portions 238 and 239, respectively, which mate with the cylindrical surfaces 224 and 225. respectively.

Note will be taken that each vane is set the same distance in a corresponding insert in a notch therein which has a depth A3, shown in FIG. 11. The nearest vane edges are, thus, spaced distances from the crystals equal to A4, shown in FIG. 11.

As shown in FIG. 13, rod 186 may have a flat 240 for set screw 230.

Figure 15:
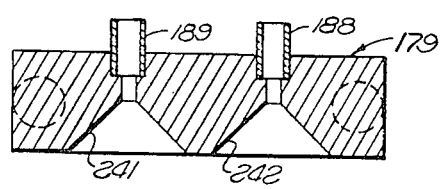
FIG. 15 is a horizontal sectional view taken on the line 15—15 shown in FIG. 14.
Figure 14:
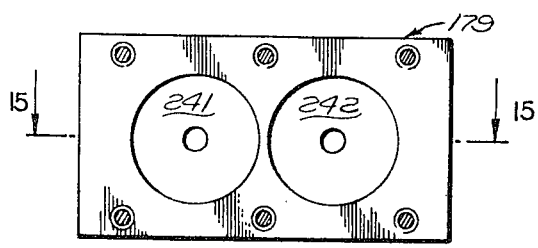
FIG. 14 is a vertical sectional view taken on the line 14—14 shown in FIG. 5.

As shown in FIGS. 14 and 15, block 179 has frusto-conical surfaces 241 and 242 partially defining spaces from which air and gas are vented to the atmosphere, respectively, through ferrules 189 and 188, respectively.

The air and gas flow into and out of block 177, shown in FIG. 5, may or may not be perfectly fluid tight, as desired. It will be noted that, when operating at very low pressures, the need for sealing, in some cases, may not practically exist.

In FIG. 11, if desired, dimension A5 may be 0.015 inch, but this dimension is not critical. Similarly, in FIG. 11, dimension A2 may be 0.03 inch, but this dimension is not critical. Surfaces 224 and 225 may have a diameter of 1 inch. Vanes 109 and 110 may each have a maximum horizontal dimension, as viewed in FIG. 11, of 1 inch. Again, the 1 inch dimension is not critical.

Assuming the foregoing dimensions, in FIG. 11, dimensions A3 would then be 0.015 inch. Dimension A4 might typically be 0.005 inch, but, again, this dimension is not critical.

Inserts 232 and 233, shown in FIG. 11, may be perfect solids of revolution except for surfaces 238 and 239. However, the inserts 232 and 233 need not be of this particular configuration. For example, insert 232 could be a solid of revolution about a horizontal axis in the plane of the drawing of FIG. 11 about which the cylindrical surface of recess 234 is concentric. Surface 238 is a portion of a surface of revolution bounded by two planes intercepting the same through the axis of chamber 227. The radius of surface 238 is, thus, one-half inch, assuming the dimensions used are those given hereinbefore. A mathematical cylinder defined by a cylindrical surface of a diameter of 1 inch would, thus, lie congruent with surfaces 238 and 239 in FIG. 11.

That portion of the apparatus shown in FIG. 11 may be considered to be, if desired, precisely symmetrical about a plane perpendicular to the drawing through the axis of rod 186. However, prefect symmetry is, of course, not a requirement. In other words, inserts 232 and 233 may be identical, although that is not required.

Vanes 109 and 110 preferably are made of Ni-Span-C, a conventional magnetic material. However, the use of this magnetic material is not critical. The material Ni-Span-C is preferred because it has a very low thermal coefficient of expansion. The material Ni-Span-C is old and well known in the art, by itself.

In FIG. 12, dimension A6 may be 1.0 inch, if desired. However, this dimension is not critical.

Each of the vanes 109 and 110 may have a thickness of 0.010 inch, although this thickness is not critical. If desired, vanes 109 and 110 may be silver soldered to inserts 233 and 232, respectively, in slots slightly larger than 0.010 inch. Such insert slots are preferably no larger than is necessary to permit an easy sliding fit of the vanes thereinto.

Preferably, the free vibratable ends of vanes do not touch the contiguous surfaces of block 177.

All gas and air connections herein, if desired, may be made with any conventional sealant such as that sold under the trademark, "Locktite," but as explained previously, this is not necessarily required.

THE ALTERNATIVE TWIN CELL ASSEMBLY 503 ILLUSTRATED IN FIGS. 16–20

Figure 16:
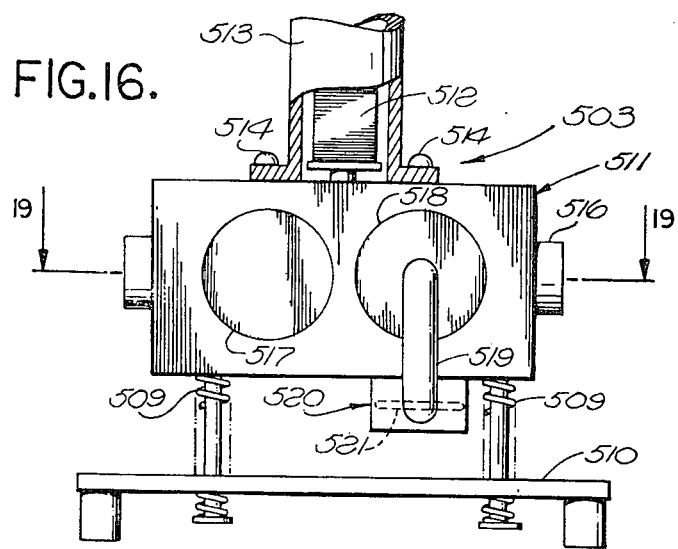
FIG. 16 is a rear elevational view of an alternative gravity cell constructed in accordance with the present invention.

An alternative gravity cell 503 is shown in FIG. 16 and is mounted resiliently on springs 509 relative to a fixed plate 510. Cell 503 includes a block 511 which may be identical to much of the construction of blocks 177, 178 and 179 shown in FIG. 5, with these three blocks welded together in a gas tight manner.

In FIG. 16, a drive coil 512 is fixed relative to block 511, as before. Drive coil 512 has a cover 513 which is fixed to block 511 by cap screws 514.

Block 511 has projections 517, 518, 527 and 528. A connecting tube 519 exits from projection 518 and enters a thermally conductive block 520 having a slot 521 therein.

Figure 20:
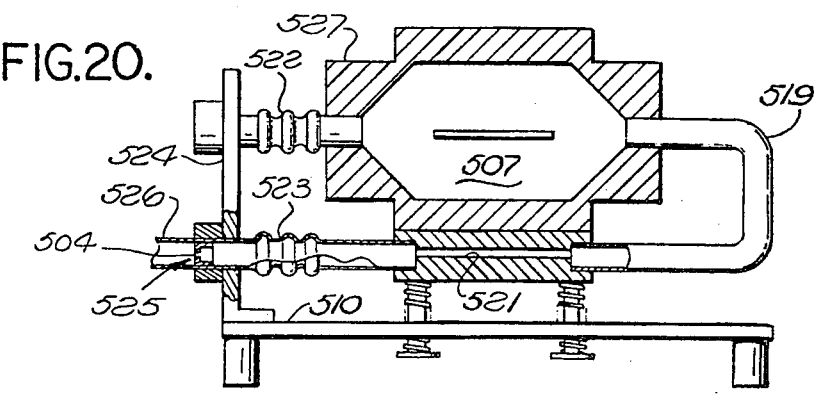
FIG. 20 is a vertical sectional view of the cell taken on the line 20—20 shown in FIG. 17.

As before, block 511, including projections 517, 518, 527 and 528, may be made of a thermally conductive metal. The same is true of block 520. As shown in FIG. 20, tube 519 being hollow, the chamber 507 is filled with gas through a flexible bellows 522. This gas is circulated through tube 519, slot 521 and out through flexible bellows 523. The left ends of bellows 522 and 523 are mounted on a plate 524. Plate 524, in turn, if fixed relative to plate 510.

Figure 17:
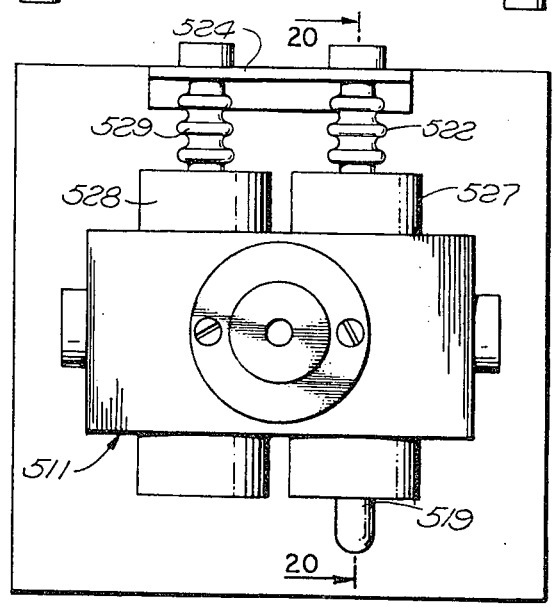
FIG. 17 is a top plan view of the cell shown in FIG. 16.
Figure 18:
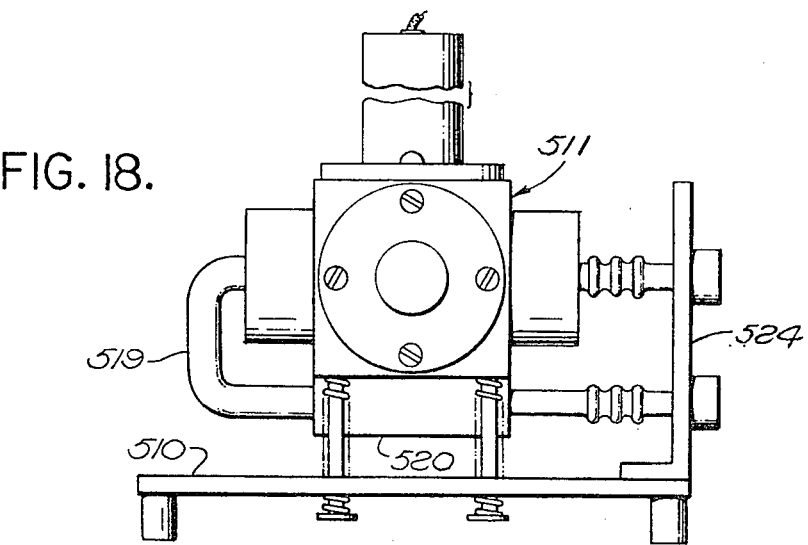
FIG. 18 is a side elevational view of the cell shown in FIG. 17.

As shown in FIG. 17, projections are provided at 527 and 528.

In FIG. 17, a flexible bellows 529 is connected from plate 524 to projection 528. See also FIG. 19.

Figure 19:
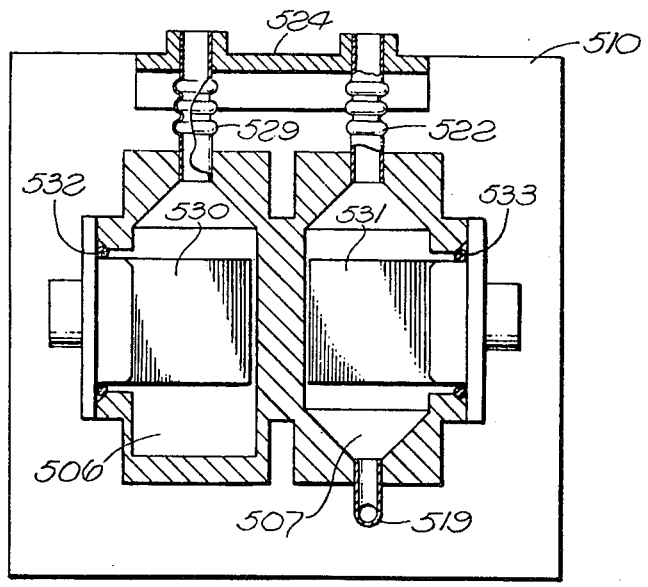
FIG. 19 is a transverse sectional view of the cell taken on the line 19—19 shown in FIG. 16.

In FIG. 19, the gas chamber 507 and the air chamber 506 are shown. Cantilever leaf spring vanes 530 and 531 are vibrated in a manner identical to the manner in which vanes 109 and 110 are vibrated. Moreover, the size and shape of vanes 530 and 531 may be identical to those of vanes 109 and 110. The same is true of their mountings, except that gas tight seals are provided by O-rings 532 and 533, respectively.

THE PREAMPLIFIER OF FIG. 21

Figure 21:
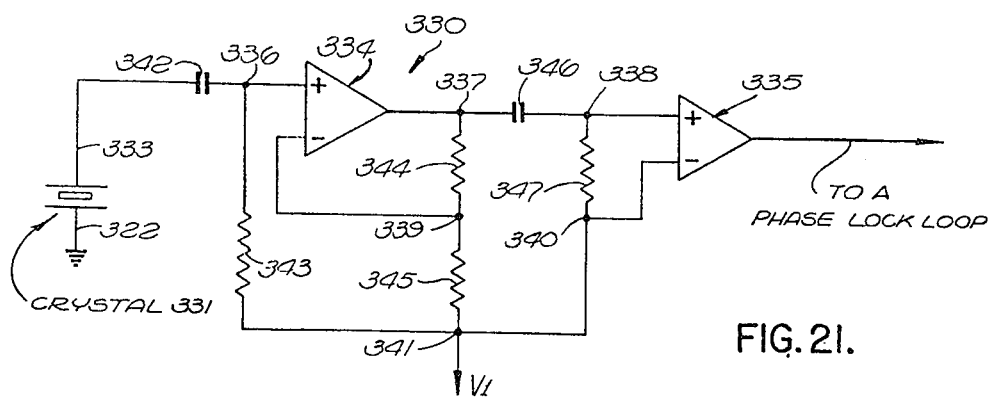
FIG. 21 is a schematic diagram of a preamplifier shown in FIG. 4.

A preamplifier 330 is illustrated in FIG. 21 including a piezoelectric crystal 331 having one side grounded at 322 and an output lead 333. Differential amplifiers are illustrated at 334 and 335. Junctions are provided at 336, 337, 338, 339, 340 and 341. Junction 341 is connected to potential V1. A typical value for V1 is 2.5 volts. A typical value for V2, referred to hereinafter, is 24.0 volts.

A capacitor 342 is connected from lead 333 to junction 336. Junction 336 is connected to the noninverting input of amplifier 334. A resistor 343 is connected between junctions 336 and 341. The inverting input of amplifier 334 is connected from junction 339. The output of amplifier 334 is connected to junction 337. A resistor 344 is connected between junctions 337 and 339. A resistor 345 is connected between junctions 339 and 341. Junctions 340 and 341 are connected together. The inverting input of amplifier 335 is connected from junction 340. A capacitor 346 is connected between junctions 337 and 338. A resistor 347 is connected between junctions 338 and 340. The noninverting input of amplifier 335 is connected from junction 338. The output of amplifier 335 is then connected to a phase lock loop. Crystal 331 may be crystal 112 or crystal 111. Each of the preamplifiers 316 and 317 may, if desired, be identical to preamplifier 330 shown in FIG. 21.

THE POWER AMPLIFIER 304 OF FIG. 22

Figure 22:
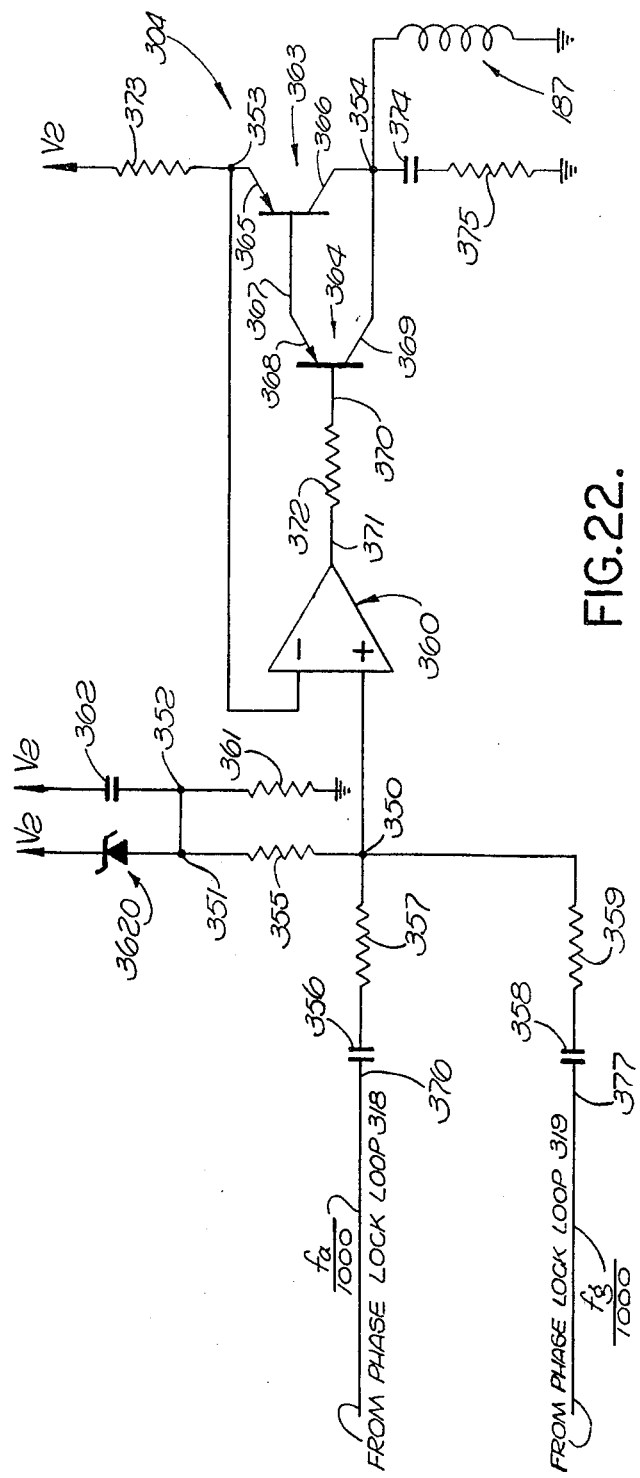
FIG. 22 is a schematic diagram of a power amplifier illustrated in FIG. 4.

A schematic diagram of the power amplifier 304 is shown in FIG. 22. Power amplifier 304 does more than merely amplify the input signals thereto, as will be explained now and hereinafter.

As shown in FIG. 4, power amplifier 304 has input leads 376 and 377 which are also shown in FIG. 22. Junctions are provided at 350, 351, 352, 353 and 354. Junctions 350 acts as a summing junction. It sums the square waves appearing on leads 376 and 377, and a D.C. voltage which may or may not vary due to the flow of current through a resistor 355 connected between junctions 350 and 351. A capacitor 356 and a resistor 357 are connected in succession in series in that order from lead 376 to junction 350. Similarly, a capacitor 358 and a resistor 359 are connected in succession in series in that order from lead 377 to junction 350. A differential amplifier is provided at 360 having its noninverting input connected from junction 350.

Junctions 351 and 352 are connected together. A resistor 361 is connected from junction 352 to ground. A capacitor 362 is connected from junction 352 to potential V2. A zener diode 3620 is connected from junction 351 to potential V2.

Transistors are provided at 363 and 364. Transistor 363 has an emitter 365, a collector 366 and a base 367. Transistor 364 has an emitter 368, a collector 369 and a base 370.

Amplifier 360 has an output lead 371. A resistor 372 is connected from lead 371 to transistor base 370. The inverting input of amplifier 360 is connected from junction 353. Emitter 365 is also connected from junction 353. A resistor 373 is connected from junction 353 to a point of potential V2.

Collector 366 is connected to junction 354. Base 367 is connected to emitter 368. Collector 369 is also connected to junction 354.

A capacitor 374 and a resistor 375 are connected in succession in series in that order from junction 354 to ground. Driver coil 187 is connected from junction 354 to ground.

The current through resistor 355 determines the voltage thereacross and determines the D.C. current through driver coil 187. Such a D.C. current is desirable to keep air and gas vanes 110 and 109 from vibrating at frequencies twice the frequencies of the signals $f_a/1{,}000$ and $f_g/1{,}000$. Note will be taken in FIG. 11 that regardless of the direction of current in driver coil 187, when such current reaches a maximum, vanes 109 and 110 will be attracted to rod 186.

Figure 23:
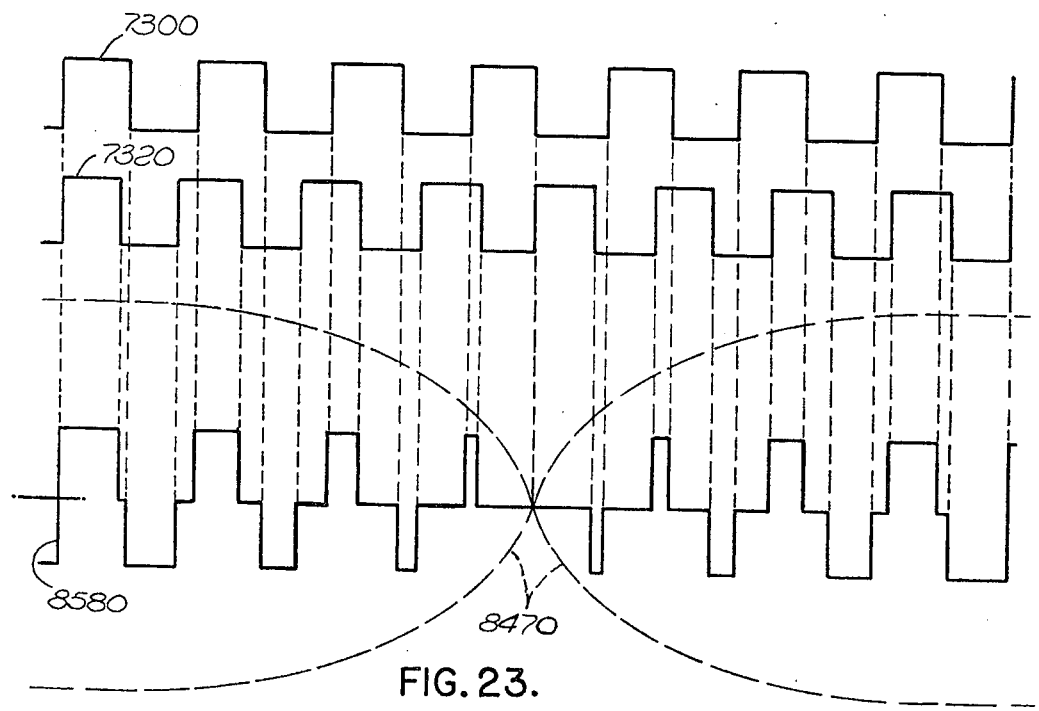
FIGS. 23 and 24 are graphs of waveforms characteristic of the operation of the power amplifier.

In FIG. 23, square waves 7300 and 7320 at the outputs of dividers 302 and 303, respectively, are indicated. When square waves 7300 and 7320 are added together, the waveform 8580 is obtained. From the following Fourier analysis of the waveform 8580, by inspection, the envelope 8470 of the fundamental may appear as shown in dotted lines in FIG. 23.

Figure 24:
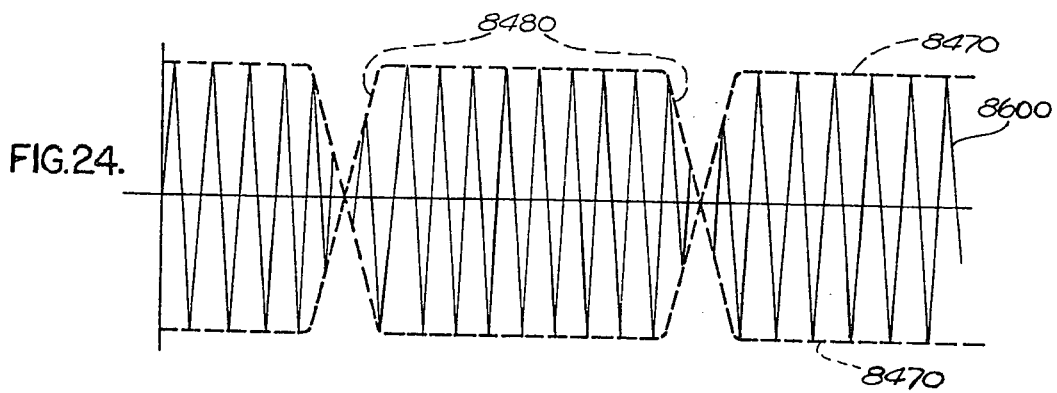

The envelope 8470 is again shown in FIG. 24 with a fundamental carrier 8600.

In FIG. 5, the outputs of dividers 302 and 303 are square waves. That is, they are perfectly square. The mark-to-space ratio is substantially equal to unity in each case. The frequency of one may or may not be slightly different from the other. The same is true of their pulse widths. However, the square wave amplitude in each case is the same.

It is well known that the Fourier analysis of a square wave yields $$y_o = \frac{4E_o}{\pi}(\cos x_o - \frac{1}{3}\cos 3x_o$$
$$+ \frac{1}{5}\cos 5x_o - \frac{1}{7}\cos 7x_o + \ldots \quad (24)$$

where,
$x_o = 2\pi f_o t$,
$\pi = 3.14159$
$f_o$ is frequency, and
$t$ is time.

The Fourier analysis of the output of the air input circuit yields $$y_a = \frac{4E}{\pi}(\cos x - \frac{1}{3}\cos 3x + \ldots) \quad (25)$$

where,
$x = 2\pi f t$, and
$f$ is, for example, 314 Hz.

The Fourier analysis of the output of the gas input circuit yields $$y_g = \frac{4E}{\pi}(\cos kx - \frac{1}{3}\cos 3kx + \ldots) \quad (26)$$

where,
$k = 1 \pm \Delta$, and
$\Delta$ is in the range 0.003 to 0.01.
Using the trigonometric identify, $$\cos u + \cos v = z \cos \frac{u+v}{z} \cos \frac{u-v}{z} \qquad (27)$$

$$y_a + y_a = \frac{8E}{\pi} \cos \frac{x+kx}{z} \cos \frac{\mp \Delta x}{z}$$

$$- \frac{1}{3} \cos \frac{3x+3kx}{2} \cos \frac{\mp 5\Delta x}{2}$$

$$+ \frac{1}{5} \cos \frac{5x+5kx}{2} \cos \frac{\mp 5\Delta x}{2}$$

$$- \frac{1}{7} \cos \frac{7x+7kx}{2} \cos \frac{\mp 7\Delta x}{2} + \ldots \qquad (28)$$

Note that the driver coil may have an inductive reactance given by $$X_L = 2\pi f_m L \qquad (29)$$

where

L is the inductance, and $f_m = f = kf/2$.
The term $f_m$ is the fundamental carrier.
Note, $$\frac{x+kx}{2} = \frac{x(1+k)}{2} \times 2\pi ft \times \frac{1+k}{2}$$

$$= 2\pi t \times \frac{f+kf}{2} \qquad (30)$$

Note that the amplitude of the third harmonic is one-third that of the fundamental. However, the inductive reactance of the driver coil triples for the third harmonic, $3f_m$. Thus, the driver coil current may be, more or less, only about 11 percent of the fundamental amplitude. It is, thus, possible to use square waves rather than sine waves at the outputs of the input circuits without disturbing the resonant operation of the device as two combined electromechanical oscillators. Moreover, the circuit is more economical to construct because the square waves are used.

It is important to note two things:
1. There are no even harmonics.
2. All odd harmonics go to zero when the fundamental goes to zero.

This means that a sharp notch in the envelope is created. The notches are shown at 8480 in FIG. 24. The notches 8480 may be much deeper than as shown in FIG. 24. This provides for exceptionally good monitoring of the fundamental envelope frequency.

Not only do the terms cos 3x, cos 5x, etc., go to zero when cos x = 0, the terms cos 3 x, /2, cos 5 x, /2, etc., go to zero when cos x/2 = 0. That is, not only the odd harmonics all go to zero at the same time, their envelopes all go to zero at the same time as well.

Throughout this description, reference will be made to the text of certain U.S. patents and U.S. patent applications. These patents and patent applications are listed for convenience forthwith.

Reference is hereby made to the following patents:
1. U.S. Pat. No. 3,677,067.
2. U.S. Pat. No. 3,706,220.
3. U.S. Pat. No. 3,738,155.
4. U.S. Pat. No. 3,741,000.
5. U.S. Pat. No. 3,783,259.

The foregoing patents of paragrapsh (1), (2), (3), (4) and (5) are hereinafter referred to as patents P1, P2, P3, P4 and P5, respectively.

Reference is hereby made to the following U.S. patent applications: 1. U.S. patent application Ser. No. 265,327 filed June 22, 1972, for METHOD OF AND APPARATUS FOR PRODUCING ANALOGS AND FLOWMETERS INCORPORATING GRAVITOMETERS by G. L. Schlatter and C. E. Miller, now U.S. Pat. No. 3,862,568.

2. U.S. patent application Ser. No. 321,662 filed Jan. 8, 1973, for PULSE TRAIN MODIFICATION CIRCUIT by P. Z. Kalotay and G. A. Fitzpatrick, now U.S. Pat. No. 3,823,310.

3. U.S. patent application Ser. No. 517,212 filed Oct. 23, 1974, for GRAVITOMETERS by G. L. Schlatter and C. E. Miller.

Figure 26:
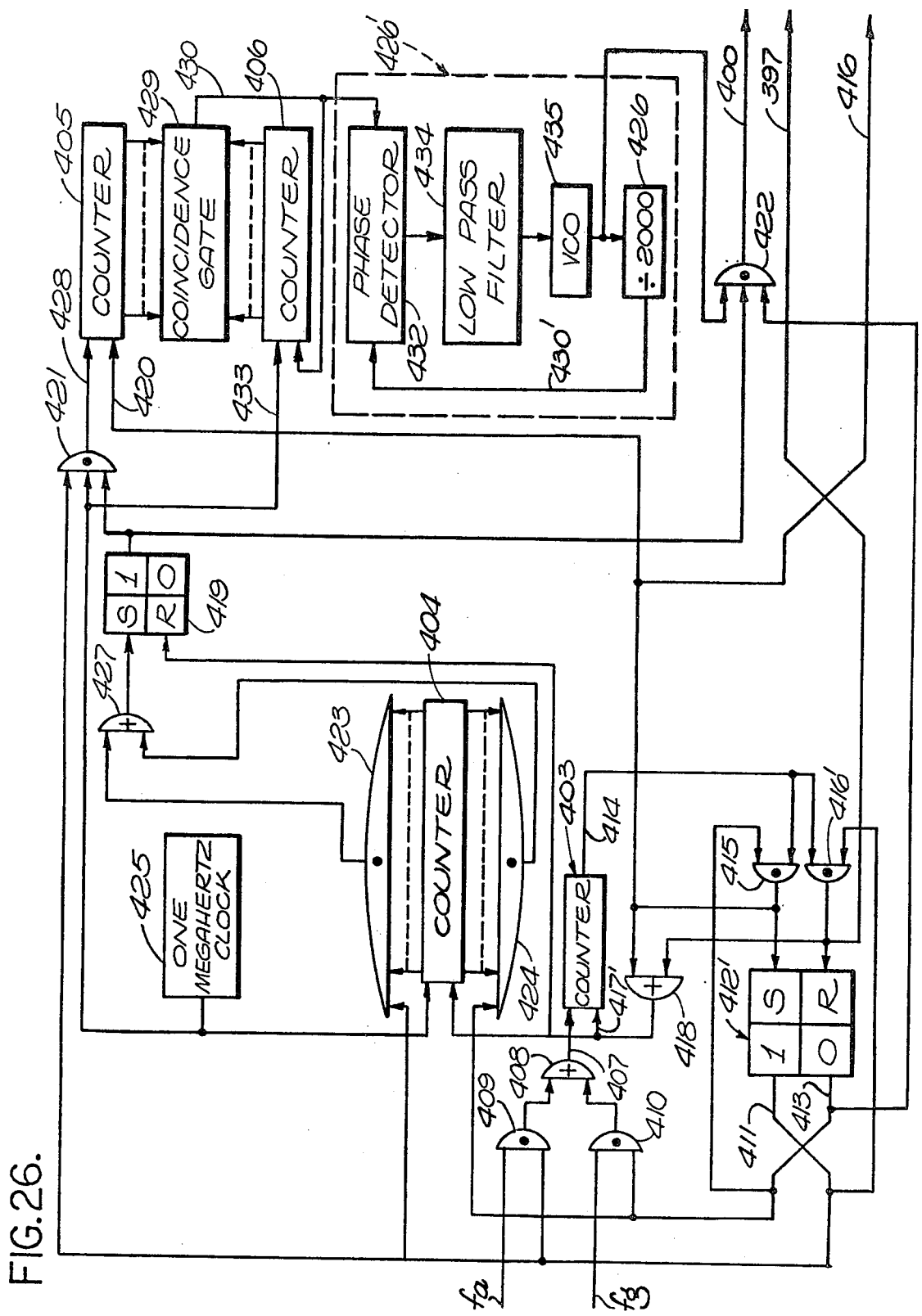
FIG. 26 is a detailed block diagram of the calculator shown in FIG. 25.

Calculator 401 is illustrated in greater detail in FIG. 26. Calculator 401 includes a counter 403, a second counter 404, a third counter 405 and a fourth counter 406.

Counter 403 has an input 407 from the output of an OR gate 408.

OR gate 408 receives inputs from the outputs of two AND gates 409 and 410. AND gate 409 receives $f_a$ pulses at one input. The other input to AND gate 409 comes from the "1" output 411 of a cycle flip flop 412'.

AND gate 410 receives $f_a$ input pulses, and an input from the "0" output 413 of cycle flip flop 412'.

Counter 403 has a reset output 414 that is connected to one input of each of two AND gates 415 and 416'.

AND gate 415 receives another input from the "0" output of cycle flip flop 412'.

AND gate 416' receives an additional input from the "1" output of cycle flip flop 412'.

The output of AND gate 415 sets cycle flip flop 412' to the "1" state. The output of AND gate 416' resets cycle flip flop 412'.

The outputs of AND gates 415 and 416' are impressed upon a reset input 417' of counter 403 through an OR gate 418. The output of OR gate 418 also resets counter 404 and a delta flip flop 419.

Figure 27:
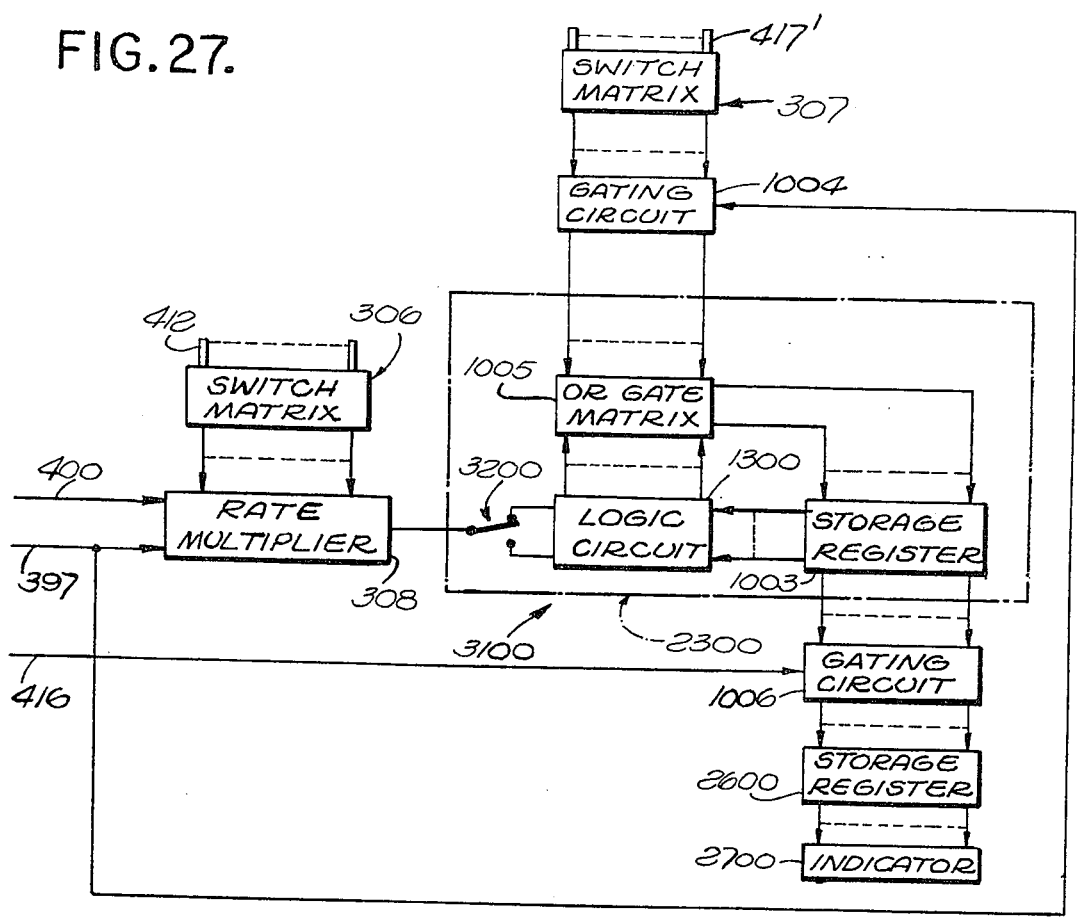
FIG. 27 is a detailed block diagram of the readout circuit shown in FIG. 25.

The output of AND gate 415 is also connected to a reset input 420 of counter 405 and to a lead 416 to a gating circuit 1006 shown in FIG. 27.

The output of AND gate 416' is connected to a lead 397 which, in turn, is connected to the reset input of a rate multiplier 308 and to a gating circuit 1004 shown in FIG. 27.

AND gates are provided at 421 and 422, the output of AND gate 422 being connected to a lead 400 which, in turn, is connected to the input of rate multiplier 308 shown in FIG. 27.

The "0" output of cycle flip flop 412' is connected to one input of AND gate 422.

Counter 404 has AND gates 423 and 424 connected therefrom to produce output pulses at predetermined counts of counter 404. The "0" output of cycle flip flop 412' is provided as one additional input to AND gate 424.

The "1" output of cycle flip flop 412' is also connected as an additional input to AND gate 423.

The "1" output of cycle flip flop 412' is connected also as an input to AND gate 421.

A one megahertz clock 425 is connected as an input to counter 404, as an input to AND gate 421, and as an input to counter 406. A divider 426 is also provided. Divider 426 divides by 2,000. Divider 426 is a portion of a conventional frequency multiplier 426'.

The outputs of AND gates 423 and 424 are impressed upon the set input of flip flop 419 through an OR gate 427. Flip flop 419 is reset by the output of OR gate 418.

The "1" output of flip flop 419 is connected as an input both to AND gate 421 and to AND gate 422.

Counter 405 has a count input 428 connected from the output of AND gate 421.

The register outputs of counters 405 and 406 are connected to a coincidence gate 429. When the count in counter 406 is exactly the same as the number stored in a register of counter 405, coincidence gate 429 produces an output pulse on a lead 430 which is connected to a reset input 431 of counter 406, and to a phase detector 432 in multiplier 426'.

Counter 406 has a count input 433.

A low pass filter 434 and a voltage controlled oscillator (VCO) 435 are also provided. Phase detector 432, low pass filter 434 and VCO 435 are connected in succession in that order from lead 430 to the input of divider 426. The output of divider 426 is connected at 430' to the other input of phase detector 432. The output of VCO 435 is also connected as another input of AND gate 422.

Coincidence gate 429 may contain any number of AND gates and OR gates. A number of such gates are shown in FIG. 28 adequate for four corresponding pairs of binary stages or flip flops in counters 405 and 406.

Counter 405 includes a register 436 having flip flops 437, 438, 439 and 440.

Counter 406 has a register 441 including flip flops 442, 443, 444 and 445.

The 37 0" outputs of flip flops 437 and 442, of the same significant digit, are connected as inputs to an AND gate 446. Similarly, the "1" outputs of flip flops 437 and 442 are connected as inputs to an AND gate 447. The outputs of AND gates 446 and 447 are connected to one input of an AND gate 448 via an OR gate 449. In similar fashion, each corresponding pair of flip flops has an OR gate and two AND gates, the connections of which are identical to those of gates 446, 447 and 449. Thus, when the number contained in register 441 is identical to the number contained in register 436, AND gate 448 produces an output pulse on lead 430 shown in FIGS. 26 and 28.

Figure 29:
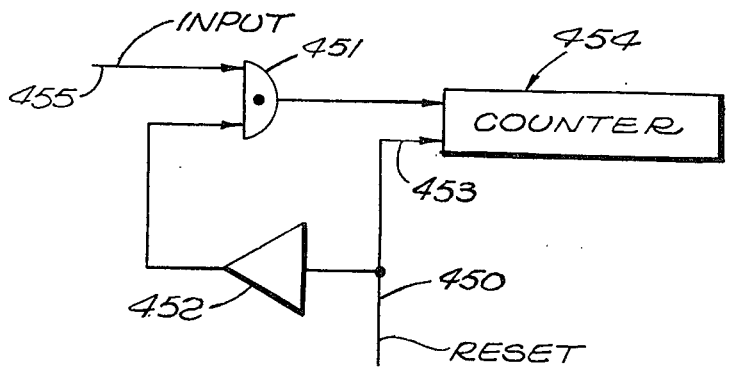
FIG. 29 is a block diagram of a counter reset circuit.

Although the digital arrangements illustrated and described herein may be employed, many, many variations thereof may be employed. If desired, a counter input may be disabled during reset. This is illustrated in FIG. 29 where a reset input lead 450 is connected to one input of an AND gate 451 through an inverter 452, and directly to a reset input 453 of a counter 454. Thus, if input pulses are supplied over a lead 455 connected to another input of AND gate 451, the output of inverter 452 disables AND gate 451 during reset.

The aforesaid U.S. patent applications (1), (2) and (3) are referred to hereinafter as applications L1, L2 and L3, respectively.

Digital computer 328 and utilization means 329 may be redrawn as calculator 401 and readout circuit 402 in FIG. 25.

Circuit 402 is shown in FIG. 27. An indicator 2700 is connected from the output of calculator 401. Circuit 402 may be decimal or binary. The indicator 2700 may be a simple indicator with one lamp for each binary stage or a binary coded decimal (BCD) indicator. Indicator 2700 may be entirely conventional. Circuit 402 may be entirely conventional or any of the types disclosed in copending application Ser. No. 423,409 filed Dec. 10, 1973, for DENSITOMETER by G. L. Schlatter, now U.S. Pat. No. 3,878,374 and assigned to the assignee of this application. The entire contents of said copending applications L1, L2 and Ser. No. 423,409 are incorporated herein hereat by this reference hereto.

Circuit 402 in FIG. 27 produces a binary or a binary coded decimal output so that indicator 2700 may be read directly, binary or decimal, in specific gravity G, where $$G = KN_a + B \qquad (31)$$

$K$ is the setting of switch matrix 306 and $N_a$ is the number of input pulses to rate multiplier 308 received in a group over lead 400.

The constant $B$ is the setting of switch matrix 307. The constant $B$ may be zero after factory calibration. The constants $K$ and $B$ are employed for convenience in field calibration. The constant $B$ apparatus may be eliminated in some cases.

The constant $B$ may be positive or negative. The position of a switch 3200 in FIG. 27 determines whether a counter 2300 counts up ($B$ positive) or down ($B$ negative).

A main storage register 1003 is illustrated in FIG. 27. As will be described, a predetermined number $B$ is entered in storage register 1003 periodically.

A logic circuit is provided at 1300. Logic circuit 1300 has an input from rate multiplier 308 through switch 3200.

In FIG. 27, the said predetermined number $B$ is periodically entered in storage register 1003. The magnitude of the predetermined number $B$ may be selected or changed by operating binary or binary coded decimal switches which are located in a switch matrix 307. The switches in matrix 307 are either connected from a positive potential or ground. The outputs of the switches are sampled and impressed upon storage register 1003 periodically. A gating pulse is impressed upon a gating circuit 1004 for this purpose.

Gating circuit 1004 is connected from matrix 307 to an OR gate matrix 1005. The output of OR gate matrix 1005 is then impressed upon storage register 1003.

Once the said predetermined number $B$ has been entered into storage register 1003, logic circuit 1300 then controls the register 1003 to count up or down depending upon whether the algebraic sign of $B$, switch 3200 in FIG. 27, is placed in the one or the other corresponding positions thereof, respectively, on this account. The output of logic circuit 1300 is, thus, impressed upon storage register 1003 through OR gate matrix 1005. Logic circuit 1300 receives pulses to count from switch 3200. Logic circuit 1300 receives other inputs from storage register 1003.

From the foregoing, it will be appreciated that matrix 1005 with logic circuit 1300 and storage register 1003 form either a count up counter or a count down counter depending upon in which position switch 3200 lies. This counter may be entirely conventional, if desired.

The output of storage register 1003 is also sampled periodically by a gating circuit 1006 which may be of the same type as gating circuit 1004. Gating circuit 1006 receives pulses over a lead 416 to cause it to sample the output of register 1003. The output of gating circuit 1006 is impressed upon a storage register 2600. The output of the storage register 2600 is impressed upon indicator 2700.

If desired, indicator 2700 may be a finary or a binary coded decimal indicator.

All of the structures 1003, 1300, 307, 1004, 1005, 1006, 2600 and 2700 may be entirely conventional or may or may not be identical to the corresponding structures disclosed in U.S. Pat. No. 3,775,597.

Alternatively, indicator 2700 may simply be a row of lamps each connected from the "1" output of each of the flip-flops in storage register 2600.

Reset pulses are supplied to rate multiplier 308 and gating circuit 1004 over a lead 397.

The purpose of the switch matrix 307 is to set, periodically, the flip flops in storage register 1003 to selected states.

Switch matrix 307 may have one double-pole, double-throw switch for each bit or flip flop in register 1003. Gating circuit 1004 may have an AND gate for the set "1" and set "0" inputs to each bit or flip flop in register 1003. The OR gate matrix 1005 may have an OR gate for the set "1" and set "0" inputs of each bit in register 1003.

The same outputs of the bits in register 1003 are connected both to logic circuit 1300 and to gating circuit 1006.

OPERATION

In the operation of the present invention, $f_a$ or air pulses are supplied to AND gate 409 in FIG. 26 while $f_g$ or gas pulses are supplied to AND gate 410 in FIG. 26.

Counter 403 counts only one "kind" of pulse at a time. That is, counter 403 either counts the $f_a$ pulses or it counts $f_g$ pulses. It does not count both kinds of pulses at the same time. The pulses that counter 403 counts are determined by the state of cycle flip flop 412'. Counter 403 may have a capacity, for example, to count 100,000 pulses.

As an example, at the end of the count of a series of gas pulses, a reset pulse on the one hundred thousandth pulse on lead 414 causes cycle flip flop 412' to be set. This opens AND gate 409 and counter 403 forthwith counts the air pulses. At the same time, the pulse output of AND gate 415 passes through OR gate 418 and resets counter 404.

AND gates 423 and 424 are prewired according to the air vacuum and gas vacuum periods, respectively.

In accordance with the foregoing, the clock pulses are counted by counter 404 until AND gate 423 produces an output pulse which sets flip flop 419. This is true because AND gate 424 is disabled by the low input thereto from the "0" output of cycle flip flop 412'.

Because the "1" output of flip flop 419 is then high as is the "1" output of cycle flip flop 412', AND gate 421 passes clock pulses. Note that clock 425 is connected to another input of AND gate 421.

When all the inputs to AND gate 421 are high, the clock pulses are impressed upon count input 428 of counter 405. In this case, counter 405 counts the clock pulses. The number of clock pulses counted by counter 405 is determined by the time during which the "1" output of flip flop 419 is high, i.e. between set and reset. The reset occurs on the one hundred thousandth count of counter 403 via AND gate 416' and OR gate 418.

In accordance with the foregoing, counter 405 counts a number of clock pulses directly proportional to the difference between the air vane period and the air vane vacuum period.

The division of the pulse width of the next output pulse of the "1" output of flip flop 419 by the number stored in the register of counter 405 will now be explained.

When the output of AND gate 416' resets cycle flip flop 412', the "0" output of cycle flip flop 412' becomes high, and counter 403 counts the gas pulses because AND gate 410 supplies such pulses through OR gate 408. A similar function then happens. The "1" output of cycle flip flop 412', by being connected to an input of AND gate 423, disables AND gate 423, and it is the AND gate 424 output which sets flip flop 419.

The "1" output of flip flop 419, by being connected to an input of AND gate 422, then determines how many pulses can pass through AND gate 422 over the period during which the "1" output of flip flop 419 is high. This means that if the frequency of the output signal of VCO 435 to AND gate 422 represents one variable, and the time width of the output pulse of the "1" output of flip flop 419 represents another variable, the number of output pulses of AND gate 422 is directly proportional to the product of the two variables. This is exactly what happens. However, in order for this to happen, it is necessary to convert the number stored in register 436 of counter 405 to a frequency which is directly proportional to the reciprocal of that number. This conversion is performed by the other structures to be described in greater detail immediately hereinafter. Counter 406 acts as a variable frequency divider and divides by the number in the register of counter 405. Multiplier 426' precisely multiplies the frequency of the output signal of gate 429 on lead 430 by the number 2000.

The number stored in the registers 436 and 441 of counters 405 and 406, respectively, when identical, causes coincidence gate 429 to produce an output pulse over lead 430.

Since counter 406 always divides the output of the clock by a number which is exactly equal to the number stored in the register of counter 405, the output of coincidence gate 429 at 430 is always constant divided by the number so stored. This means that the number of output pulses of AND gate 422, during the time that the "1" output of flip flop 419 is high and the "1" output of cycle flip flop is low, is directly proportional to $$\frac{T_g - T_{go}}{T_a - T_{ao}}$$

where
$T_g = 1/f_g$
$T_{go}$ is the gas vacuum period,
$T_a = 1/f_a$ and
$T_{ao}$ is the air vacuum period
Gravity $G$ is $$G = [K] \left[ \frac{T_g - T_{go}}{T_a - T_{ao}} \right]$$

where $K$ is a constant supplied by matrix 306 and rate multiplier 308 in FIG. 27.

In accordance with the foregoing, the output of rate multiplier 308 in FIG. 27 is directly proportional to gravity.

The air vacuum frequency or vacuum period is simply determined by drawing a vacuum on the air chamber, and measuring the air vane frequency or the air vane period.

The gas vacuum frequency or gas vacuum period is determined in exactly the same way as is the air vacuum frequency or the air vacuum period.

If desired, counters 403 and 404 may both have a capacity of 330,000. Counters 405 and 406 may each have a capacity of 2000. It will be obvious to those skilled in the art that greater accuracy can be obtained by increasing the sizes of the counters.

To convert the number of pulses at the output of AND gate 422 in FIG. 26 directly to gravity, a gas of a known gravity may be employed and switch matrix 306 shown in FIG. 27 adjusted until indicator 2700 reads the known gravity.

Switch matrix 307 and its associated circuitry may be eliminated in some cases. It may be a convenience for field calibration or a slight increase in accuracy because it provides one additional degree of freedom.

Note will be taken that all or any portion of the present invention may incorporate binary or binary coded decimal devices.

The word "vacuum" as used herein may or may not be defined as a vacuum pressure which is substantially less than one atmosphere.

It is to be understood that amplifiers or inverters or the like may be added to or subtracted from the disclosure of the invention herein, as desired. For example, low pass filter 434 may or may not incorporate an amplifier.

Although a symbol has been used consistently in the drawings to represent OR gates, it is to be understood that the symbol includes, but is not limited to, a "wire" OR gate. Thus, one or more or all of the symbols employed herein to represent an OR gate may or may not be a wire OR gate, as desired.

The phrase "AND gate," as used herein and as used in the claims, is hereby defined to include a NAND gate with or without an inverter, and vice versa.

The phrase "OR gate," as used herein and as used in the claims, is hereby defined to include a NOR gate with or without an inverter, and vice versa.

All of the said patents P1, P2, P3, P4 and P5 are hereby incorporated herein by this reference hereto as though fully set forth herein hereat.

The said L1 application is, by this reference hereto, hereby incorporated herein as though fully set forth herein hereat.

Indicator 2700 may be entirely conventional. For example, it also may be one sold by the Burroughs Corporation under the trademark PLANAPLEX.

All rate multipliers disclosed herein may be entirely conventional. Any one including, but not limited to, those sold by Motorola Semi-Conductor Products, Inc. and Texas Instruments Incorporated may be employed. The Motorola model numbers are MC 14527AL and MC 14527CL. The Texas Instruments rate multipliers are described as synchronous rate multipliers with circuit types SN7497 and SN74167. The foregoing Motorola and Texas Instruments model numbers are generally given for what is described herein as a "rate multiplier decade" which may be connected seriatim ad infinitum, if desired.

As stated previously, circuit 402 in FIG. 27 may be entirely conventional. One or many such circuits may be employed. One such circuit is sold as an MOS by Hughes Aircraft Company. This MOS is described further as a counter/latch/decoder/driver HCTRO107D/HCTRO107F.

Alternatively, a portion of or all of the digital structures disclosed herein may be BCD or binary.

The word "fluid" is hereby defined to mean a gas or liquid, when applicable.

The word "gravitometer" is not necessarily limited to an instrument for producing an output directly proportional to the density of a sample gas to air or the density of a sample liquid to water; or the density of a sample fluid, liquid or gas, to any reference fluid, liquid or gas.

The word "gravitometer" is hereby defined for use herein and for use in the claims as are the other definitions herein, as a device for producing either an analog or digital output directly proportional to gravity with or without utilization means including, but not limited to, a voltmeter calibrated in density, a process controller, a flowmeter, a digital indicator or any other device or system.

The word "gravity" is hereby defined for use herein and for use in the claims as the output of a gravitometer and is not limited in definition any more than the word "gravitometer" is limited by the definitions herein. Moreover, the word "gravity" is as broad as the broadest definition of "gravitometer" herein.

The phrase "rate multiplier" is hereby defined for use herein and for use in the claims to mean a counter of any radix including, but not limited to, a binary coded decimal or decimal counter having one or preferably four stages or decades resetting on the ten thousandth count.

All the definitions set forth hereinbefore and hereinafter are for use herein and for use in the claims.

The phrase "rate multiplier" is hereby defined to include, but not be limited to, all stages or decades in any BCD or binary counter employing more than one stage or decade.

The clock disclosed herein may include crystal controlled oscillators which produce square wave output signals with or without the use of internal or external squarers.

What is claimed is:

1. A rate divider comprising: a storage register having a plurality of stages; a counter having a plurality of stages and having count and reset inputs; a coincidence gate having an output and having plural inputs connected from the stages of both said storage register and said counter for producing an output pulse at said output thereof when the number stored in said counter becomes equal to the number stored in said storage register; clock means having an output signal frequency and an output connected to said counter count input, said coincidence gate having an output signal of a frequency equal to the clock means frequency divided by the number stored in said register, said coincidence gate also being connected to the reset input of said counter; and means to change the number stored in said storage register, said register and said counter each including a plurality of flip flops each having a "0" output and a "1" output, said coincidence gate including a first AND gate for each significant digit to be used, each said first AND gate having an input connected from a "0" output of a corresponding flip flop representing one significant digit in said storage register and another input connected from the "0" output of a corresponding flip flop representing the same significant digit in said counter, said coincidence gate also including a second AND gate for each significant digit to be used, each said second AND gate having an input connected from the "1" output of a corresponding flip flop representing one significant digit in said storage register and another input connected from a "1" output of a corresponding flip flop representing the same significant digit in said counter, each of said first and second AND gates having an output, said coincidence gate including an OR gate for each pair of AND gates corresponding to one significant digit, each OR gate having an output and inputs connected from the outputs of each corresponding pair of AND gates, said coincidence gate also including a third AND gate having an output and an input from each OR gate output, said third AND gate output being connected to said counter reset input, said coincidence output signal appearing at the output of said third AND gate.

* * * * *